US007605922B2

(12) United States Patent
Willing et al.

(10) Patent No.: US 7,605,922 B2
(45) Date of Patent: Oct. 20, 2009

(54) METHOD AND GAS SENSOR FOR PERFORMING QUARTZ-ENHANCED PHOTOACOUSTIC SPECTROSCOPY

(75) Inventors: Bert Willing, Blonay (CH); Markus Kohli, Grandson (CH); Andreas Seifert, Grandson (CH)

(73) Assignee: IR Microsystems SA, Lausanne (CH)

( * ) Notice: Subject to any disclaimer, the term of this patent is extended or adjusted under 35 U.S.C. 154(b) by 151 days.

(21) Appl. No.: 11/970,570

(22) Filed: Jan. 8, 2008

(65) Prior Publication Data
US 2009/0027677 A1 Jan. 29, 2009

(30) Foreign Application Priority Data
Jul. 24, 2007 (EP) .................................. 07014498

(51) Int. Cl.
*G01J 3/30* (2006.01)
*G01N 21/00* (2006.01)
(52) U.S. Cl. .................. 356/437; 356/440; 356/317
(58) Field of Classification Search ......... 356/432–444, 356/450–458
See application file for complete search history.

(56) References Cited

U.S. PATENT DOCUMENTS

| | | | | |
|---|---|---|---|---|
| 3,911,276 A | * | 10/1975 | Bell | 250/343 |
| 4,058,725 A | * | 11/1977 | Aine | 250/343 |
| 5,159,411 A | * | 10/1992 | Hammerich et al. | 356/432 |
| 6,182,499 B1 | * | 2/2001 | McFarland et al. | 506/12 |
| 7,245,380 B2 | * | 7/2007 | Kosterev | 356/437 |
| 7,387,021 B2 | * | 6/2008 | DiFoggio | 73/152.55 |
| 2005/0117155 A1 | | 6/2005 | Kosterev | |
| 2006/0266109 A1 | * | 11/2006 | DiFoggio | 73/152.55 |

FOREIGN PATENT DOCUMENTS

EP 1 750 116 2/2007

OTHER PUBLICATIONS

European Search Report for corresponding Application No. 07 01 4498 dated Nov. 22, 2007.
Kosterev Anatoliy et al.; "Applications of 1-10 quartz tuning forks in spectroscopic gas sensing"; Review of Scientific Instruments, American Institute of Physics, U.S., vol. 76, No. 4, Mar. 23, 2005, pp. 43105-43105; XP012079295.

* cited by examiner

*Primary Examiner*—Gregory J Toatley, Jr.
*Assistant Examiner*—Jarreas C Underwood
(74) *Attorney, Agent, or Firm*—Renner, Otto, Boisselle & Sklar, LLP

(57) ABSTRACT

A method for performing quartz-enhanced photoacoustic spectroscopy of a gas, includes providing a light source configured to introduce a laser beam having at least one wavelength into the gas such said at least one molecule within in the gas is stimulated generating an acoustic signal, accumulating the acoustic signal in a resonant acoustic detector, generating a resonant absorption signal ($S_A$) relative to the gas concentration by at least one tuning fork serving as resonant acoustic detector, generating additionally a resonant intensity signal ($S_I$) proportional to the intensity of the laser beam travelling through the gas, and providing an output signal ($S_{GC}$) from said absorption signal ($S_A$) and said intensity signal ($S_I$) being independent of the intensity of the light relative to the presence or concentration of the gas.

11 Claims, 2 Drawing Sheets

METHOD AND GAS SENSOR FOR PERFORMING QUARTZ-ENHANCED PHOTOACOUSTIC SPECTROSCOPY

CROSS-REFERENCE TO RELATED APPLICATION

This application claims priority under 35 USC §119 to European Application Number 07 014 498.5, filed on Jul. 24, 2007, the entire disclosure of which is incorporated herein by reference.

BACKGROUND OF THE INVENTION

The present invention relates to a method for performing a quartz-enhanced photoacoustic spectroscopy of a gas by using a light source configured to introduce a laser beam having at least one wavelength into the gas such that at least one molecule within in the gas is stimulated generating an acoustic signal, accumulating the acoustic signal in a resonant acoustic detector and generating a resonant absorption signal relative to the gas concentration by at least one tuning fork serving as resonant acoustic detector. The invention further relates to a photoacoustic gas detector for performing a quartz-enhanced photoacoustic spectroscopy with appropriate processing means for providing a signal relative to the presence or concentration of the gas.

Such a method and gas detector are disclosed in US 2005/0117155 A1, which is incorporated in this description by reference.

In general there are three basic concepts for a photoacoustic gas sensor:

Non-Resonant Photoacoustic Gas Sensor

This concept uses a quasi-closed gas absorption cell and most often a thermal light source to measure gases in the mid-infrared. Chopping frequencies are limited by the thermal light source to no more than 100-150 Hz. The volume of the gas absorption cell is not relevant and can be minimized; the limit being contributions of dead volume in the microphone etc.

Resonant Photoacoustic Gas Sensor

For this concept, the light source is chopped at the resonant frequency of the gas absorption cell. The kHz range of cells in the cm range requires lasers as light sources, and the gas absorption cell can be open in the places of the nodes of the resonance (the microphone being placed at the anti-nodes). The advantage of such a concept is the very high rejection of ambient noise due to the high chopping frequency (ambient contributions decrease by 1/f). A limitation for this concept is the diffusion time for fast applications (typically 10-30 s).

Quartz-Enhanced Photoacoustic Gas Sensor

This concept as disclosed in US 2005/0117155 A1 replaces the resonant gas absorption cell by a resonant microphone, and the broadband microphone by a broadband volume. The absorption volume is not at all enclosed so that the sound wave generated by the gas absorption is very weak. This is counterbalanced by the extremely high quality factor of the resonant microphone. The typical approach is to use the quartz fork of a quartz wrist-watch as the resonant microphone (resonance frequency of 32,768 Hz) and the space between the prongs of the quartz fork as the absorption volume. In such a setup, the laser beam is simply focused between the prongs of the quartz fork, and the latter acts as the microphone. Apart from an extremely high diffusion rate and a minimum size (the fork is about 10 mm long and 3 mm wide), such a device is extremely cheap as quartz tuning forks are a basic component of quartz watches and produced in high quantities.

The resonant modes of a tuning fork enable an extremely high noise rejection: The sound wave of the gas absorption triggers a symmetrical vibration mode, whereas any external noise triggers an anti-symmetrical vibration mode. As both modes have slightly different frequencies with both high quality factors, the anti-symmetrical contribution is not picked up by the signal electronics.

In a photoacoustic measurement setup, a chopped light beam of a selected wavelength is fed into a gas absorption cell or volume, where its absorption by the targeted gas creates an acoustic sound wave. This sound wave is picked up by a microphone, the microphone signal being essentially proportional to the gas concentration within the gas absorption cell.

As the microphone signal is at the same time essentially proportional to the intensity of light within the gas absorption cell, a second detecting device (often an infrared detector or a photodiode) as reference signal is used to monitor the intensity of the light source over time.

In all designs of a photoacoustic gas detector, the light beam will eventually hit the structure of the gas absorption cell. The partly absorption of the light incident onto the structure creates a sound wave within the structure, this second sound wave also being picked up by the microphone at the same frequency as the gas concentration signal.

This so-called "wall noise" creates therefore an unwanted offset contribution to the microphone, and this contribution is especially important when the light source is a laser beam. Much design effort has been put in place over the last years in order to limit the contribution of the wall noise to the gas concentration measurement.

SUMMARY OF THE INVENTION

The present invention proposes a method and a gas detector for photoacoustic spectroscopy (PAS) with a reduced contribution of the wall noise to the gas concentration measurement.

According to the invention the method comprises generating a resonant intensity signal proportional to the intensity of the laser beam travelling trough the gas and providing an output signal from the absorption signal and the intensity signal being independent of the intensity of the light relative to the presence or concentration of the gas.

The wall noise is essentially proportional to the intensity of the light source, and can be thus used as the reference signal mentioned above. In the case of laser diode photoacoustic gas sensors, the use of the wall noise as intensity reference can therefore eliminate the reference photodiode, which contributes to lower cost and to smaller device sizes.

The underlying idea is to replace the photo diode normally used for laser intensity measurement by the wall noise, which is generated on a tuning fork. The wall noise generated by the laser beam incident on the tuning fork is proportional to the intensity of the laser beam, if the mechanical adjustment does not change over time. This solution targets gas sensors based on quartz-enhanced photoacoustics with a laser diode, notably for applications where a low price is crucial (e.g. automotive applications, consumer applications). By replacing the photo diode used for laser intensity the costs of the photo diode are eliminated or reduced.

Depending on the gases to be detected, there are two possibilities to the separate the wall noise signal from the gas concentration signal: According to the measurement principal in PAS the light is pulsed or modulated at a specific resonant acoustic or modulation frequency in order to produce a series of sound waves or photoacoustic signals. Accordingly, an acoustic detector mounted in acoustic communication with the environment can detect changes occurring as result of the light stimulation of the absorbing molecule concentration or signal. Because the amount of the absorbed energy is proportional to the concentration of the absorbing molecules, the acoustic signal can be used for concentration measurements. In consequence, for detecting the photoacoustic wall noise it is necessary to provide a signal having as less as possible contributions resulting from the gas. Thus, it is necessary that the laser beam mainly incidents on the tuning fork for measuring the wall noise. This can be performed by slightly detuning the light source so that no gas can be detected. This solution is only possible for gases to be detected having sharp absorption lines, e.g. carbon dioxide. For hydrocarbons, for example, which do not have sharp absorption lines, it is not possible to detune the laser source such that no gas is detected. Therefore it is necessary to use a second tuning fork for separating the wall noise signal from the gas concentration signal, which have both the same frequency at a locked phase relation. Here, the first fork has the laser beam focused between its prongs and picks up the gas concentration, and the second fork being preferably placed behind the first fork such that the laser beam mainly generates wall noise and only little or no gas concentration signal. The second fork would add costs which are considerably less than the costs of a photo diode.

As generally known, it is possible to use for detecting more than one gas within one gas sensor more than one tuning fork. Consequently, a respective number of second tuning forks for detecting the wall noise are necessary. Further, it is basically possible, to place the second tuning fork for detecting wall noise before the first tuning fork, however, this leads to intensity losses. The arrangement of the second tuning fork behind the first tuning fork is therefore a preferred solution.

In a preferred embodiment, in order to overcome slight resonance frequency differences between the forks due to fabrication, a measurement cycle would firstly tune onto the resonance frequency of the first fork to measure the gas concentration, and preferably subsequent, tune on the resonance frequency of the second fork to measure the laser intensity and to provide a reference signal. This reference frequency can be found by detecting the highest acoustic signal of the resonant microphone.

According to a further embodiment an optical window is arranged between the at least one tuning fork and the at least second tuning fork, which avoids a gas contribution signal being part of the reference signal of the second tuning fork.

According to another preferred embodiment another way is used to assure that the first tuning fork picks up a maximized gas concentration signal and a minimized wall noise contribution, and that the second tuning fork picks up a minimized gas concentration signal and a maximized wall noise. Here the laser beam is focused on a short focal length onto a spot in between the prongs of the first tuning fork and the second tuning fork is placed at a sufficient distance behind the second tuning fork. This will lead to a low light intensity between the prongs of the second tuning fork in comparison to the light intensity incident on the prongs.

Appropriate processing means being part of the photoacoustic gas detector provide a signal relative to the presence or concentration of a given gas in a detection region provided for receiving at least one sample gas. The processing means also process the absorption signal as well as the intensity signal for providing the required measurement signal.

Further features and advantages of the invention can be obtained from the following description of preferred embodiments in connection with the claims and the drawings. The single features can be realized alone or in combination in embodiments of the invention.

DETAILED DESCRIPTION OF THE INVENTION

As described above, in the present photoacoustic spectroscopy method and apparatus, the absorbed energy from a gas is accumulated in an acoustic detector. The material of the acoustic detector is a piezoelectric crystal quartz. Chemically, quartz is silicon dioxide, and, when properly cut, it will generate electric charge separations resulting in electric field or current when mechanical stress is applied to it; this is know as piezoelectricity. Since quartz deformation can be monitored directly by an electric signal, additional transducers are not needed. For this, as disclosed in US 2005/0117155 A1, for PAS quartz tuning forks are used with a resonant frequency close to 32,768 Hz. Such forks are used in quartz clocks and are therefore available at low costs.

Figure 1:
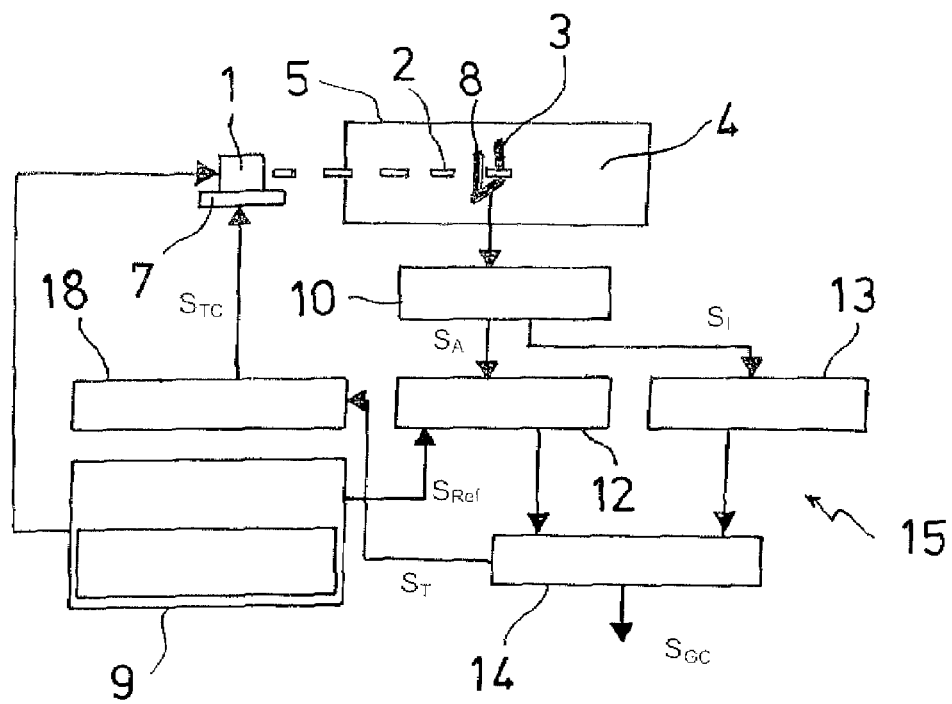
FIG. 1 a principle block diagram of a gas sensor with one fork.
Figure 2:
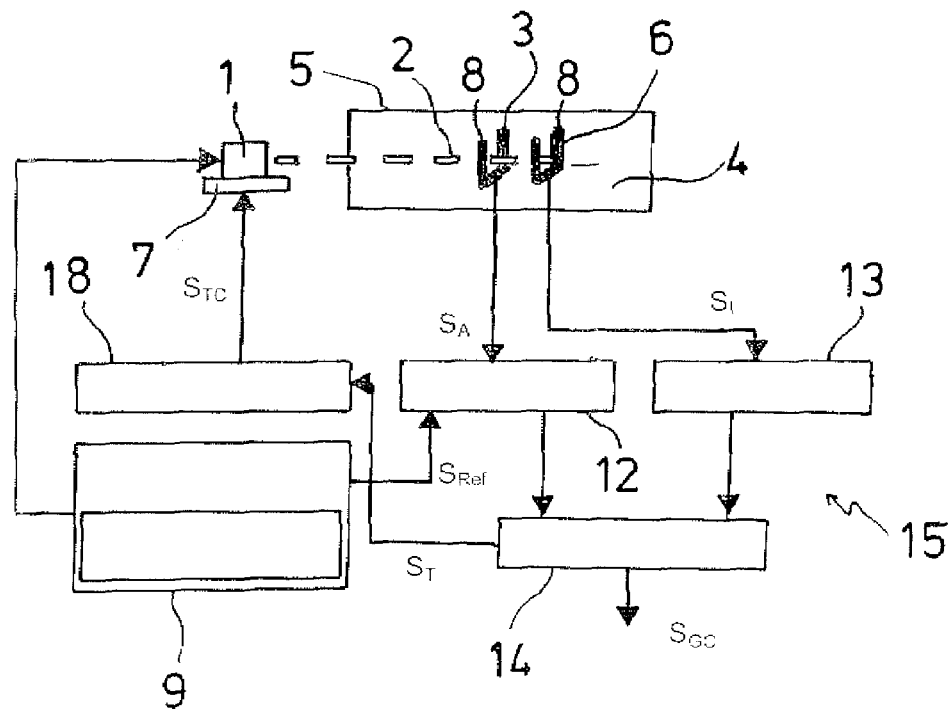
FIG. 2 a principle block diagram of a gas sensor with two forks.

FIGS. 1 and 2 show the principle of the gas sensor with processing means 15 for processing of the signals. A laser source 1, preferably a diode laser, which is in connection with temperature unit 7 acting as heater or cooler, emits light in form of a laser beam 2 through a detection region 5 providing an absorption volume 4 for a target gas to be detected. The laser source 1 is set by its temperature via the temperature unit 7, to a wavelength, which corresponds to the absorption features of interest. The drive current of the laser source 1 is modulated by a respective modulation signal provided by a frequency generator 9.

In FIG. 1 a quartz tuning fork 3 serving as acoustic detector is arranged near the absorption volume 4 with the laser beam 2 passing between the prongs 8 of the tuning fork 3. For absorption measurement, the laser source is tuned on the absorption frequency of the gas to be detected, which in turn generates a signal $S_A$ (absorption signal), which has high contributions relative to the gas absorption. For providing a reference signal, which is relative to the laser intensity, the laser source 2 is detuned so that the resonant signal $S_I$ (intensity signal) generated by the quartz tuning fork 3 has no contributions of the gas absorption. In difference to the arrangement of FIG. 1, the arrangement in FIG. 2 uses a second quartz tuning fork 6 in series with and behind of the first quartz tuning fork 3, which generates a signal relative to the laser intensity for reference. For this, the second quartz tuning fork 6 is placed such, that the laser beam 2 mainly incidents on the prongs of the quartz tuning fork. The arrangement of FIG. 1 is appropriate to detect carbon dioxide and the arrangement of FIG. 2 to detect hydrocarbons, for example.

The arrangements of FIG. 1 and FIG. 2 are similar concerning the processing means 15. As mentioned above, the quartz tuning fork 3 provides a signal $S_A$, which is proportional to the absorption of the gas in the absorption volume 4.

In the arrangement of FIG. 1 the quartz tuning fork 3 also provides the intensity signal $S_I$, which is proportional to the light intensity of the laser source 1, if the laser source is detuned. Thus, the signals from the quartz tuning fork in this arrangement are fed to synchronized switching means 10. In the arrangement according to FIG. 2 the intensity signal $S_I$ is provides by the second quartz tuning fork 6. The absorption signal $S_A$ provided by the quartz tuning fork 3 directly (FIG. 2) or via switching means 10 (FIG. 1) is fed to a lock-in-amplifier 12 for multiplying this signal with a reference signal $S_{Ref}$ received from the modulation frequency generator 9 and finally integrating of the resulting signal. The intensity signal $S_I$ from the second quartz tuning fork 6 (FIG. 2) or from the quartz tuning fork 3 via switching means 10 (FIG. 1) is fed to an amplifier 13. The signals from the lock-in-amplifier 12 and from the amplifier 13 are fed to a control unit 14. In the control unit 14 the absorption signal $S_A$ after having processed by the lock-in-amplifier 12 is normalised by dividing through the intensity signal $S_I$ from the photodiode 6 after having amplified by amplifier 14. The resulting signal $S_{GC}$ is the required signal for the concentration of the gas in the chamber 5. The control unit 14 further provides respective signals $S_T$ to the temperature control 18 to keep the laser source 1 on its temperature to a wavelength, which corresponds to the absorption features of interest.

Figure 3:
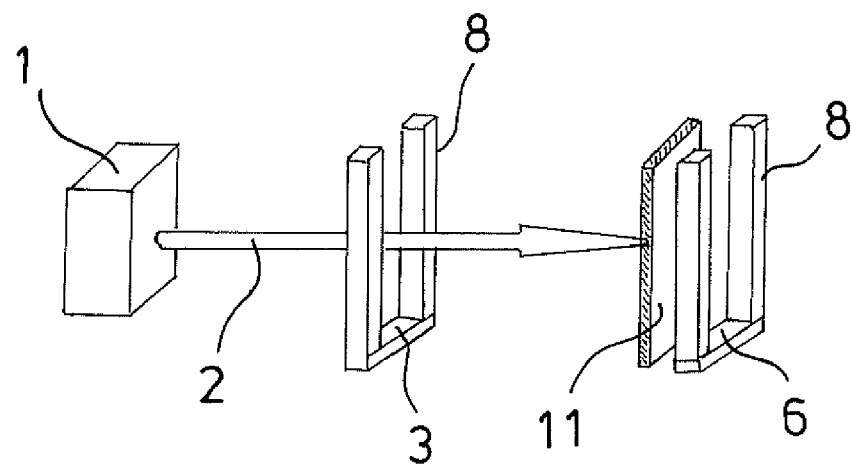
FIG. 3 a principle depiction of an embodiment with an optical window.

In the principle depiction of FIG. 3, the second quartz tuning fork 6 may be separated from the first quartz tuning fork 3 by an optical window 11, which avoids a gas contribution signal being part of the reference signal of second quartz tuning fork 6.

Figure 4:
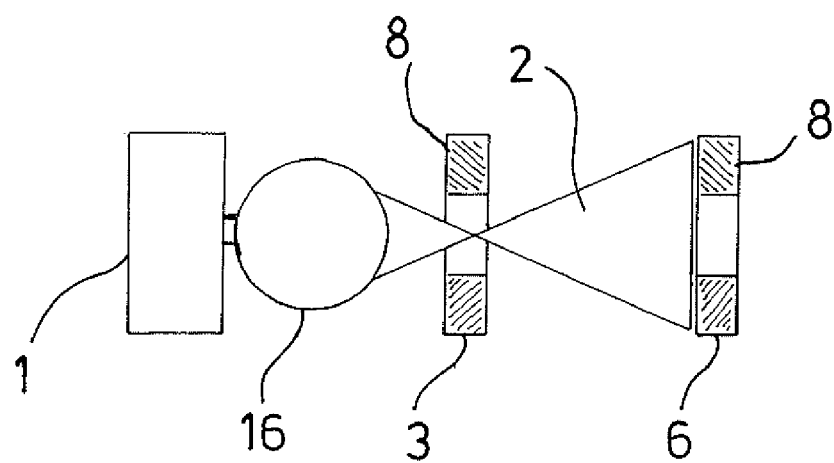
FIG. 4 a principle depiction of an arrangement for providing maximized gas concentration and minimized wall noise contribution.

Another way to assure that the quartz tuning fork 3 picks up a maximized gas concentration signal and a minimized wall noise contribution, and that the quartz tuning fork 6 picks up a minimized gas concentration signal and a maximized wall noise is shown in FIG. 4. Here the laser beam is focused on a short focal length onto a spot in-between the prongs 8 of the first tuning fork 3 by a ball lens 16. Placing the second tuning fork 6 at a sufficient distance behind the first tuning fork 3 will lead to a low light intensity between the prongs 8 of the second tuning fork 6 in comparison to the light intensity incident on the prongs 8.

The present invention targets gas sensors based on quartz-enhanced photoacoustics, notably for applications where a very low price procial. The underlying idea is to replace the photo diode normally used for laser intensity measurement by the wall noise which is generated on the tuning fork. This eliminates the costs of the photo diode. The wall noise generated by the laser beam incident on the tuning fork is proportional to the intensity of the laser beam. Depending on the gas to be measured the wall noise signal can be separated from the gas concentration signal by using only one fork or a second fork preferably behind the first fork.

Unless the context clearly requires otherwise, throughout the description and the claims, the words "comprise", "comprising" and the like are to be construed in an inclusive as opposed to an exclusive or exhaustive sense; that is to say, in the sense of "including, but not limited to".

The invention claimed is:

1. A method for performing quartz-enhanced photoacoustic spectroscopy of a gas, comprising:
providing a light source configured to introduce a laser beam having at least one wavelength into the gas such that said at least one molecule within the gas is stimulated generating an acoustic signal,
accumulating the acoustic signal in a resonant acoustic detector,
generating a resonant absorption signal ($S_A$) relative to the gas concentration by at least one tuning fork serving as resonant acoustic detector,
generating additionally a resonant intensity signal ($S_I$) proportional to the intensity of the laser beam travelling through the gas,
providing an output signal ($S_{GC}$) from said absorption signal ($S_A$) and said intensity signal ($S_I$) being independent of the intensity of the light relative to the presence or concentration of the gas,
generating said resonant absorption signal ($S_A$) by passing the light between the prongs of the said at least one tuning fork, and
generating said resonant intensity signal ($S_I$) by said at least one tuning fork by detuning the light source such that the light incidents mainly on the prongs of said at least one tuning fork.

2. A method for performing quartz-enhanced photoacoustic spectroscopy of a gas, comprising:
providing a light source configured to introduce a laser beam having at least one wavelength into the gas such that said at least one molecule within the gas is stimulated generating an acoustic signal,
accumulating the acoustic signal in a resonant acoustic detector,
generating a resonant absorption signal ($S_A$) relative to the gas concentration by at least one tuning fork serving as resonant acoustic detector,
generating additionally a resonant intensity signal ($S_I$) proportional to the intensity of the laser beam travelling through the gas,
providing an output signal ($S_{GC}$) from said absorption signal ($S_A$) and said intensity signal ($S_I$) being independent of the intensity of the light relative to the presence or concentration of the gas,
generating said resonant absorption signal ($S_A$) by passing the light between the prongs of the said at least one tuning fork, and
generating said resonant intensity signal ($S_I$) by said at least one further tuning fork arranged in series to said at least one tuning fork, now serving as first tuning fork, such said the light incidents mainly on the prongs of said at least one second tuning fork.

3. A method according to claim 2, comprising:
tuning the light source onto the resonance frequency of said at least one first tuning fork to measure the gas concentration, and
separately tuning the light source onto the resonance frequency of said at least second tuning fork to measure the laser intensity.

4. A method according to claim 2, comprising:
providing an optical window between said at least one tuning fork and said at least second tuning fork.

5. A method according to claim 2, comprising:
focusing the light beam onto a spot between the prongs of said at least first tuning fork, and
placing said at least second tuning fork behind said at least first tuning fork at a distance such said the light intensity between the prongs is low in comparison to the light intensity incident on the wall of the prongs.

6. A photoacoustic gas detector comprising:
a light source for providing a laser beam,
a detection region provided for receiving at least one sample gas,
at least one first tuning fork serving as resonant acoustic detector and providing a resonant absorption signal ($S_A$), processing means for providing a signal ($S_{GC}$) relative to the presence or concentration of a given gas in said detection region, and at least one second tuning fork arranged in series to said at least first tuning fork, said at least one second tuning fork serving as resonant acoustic detector for providing a resonant signal relative to the intensity of the laser beam travelling through said sample gas.

7. A photoacoustic gas detector according to claim 6, wherein the relative arrangement between said at least one second tuning fork and said laser beam provides mainly a resonant intensity signal ($S_I$) generated by the wall noise of the laser beam incidenting on the prongs of said at least one second tuning fork.

8. A photoacoustic gas detector according to claim 7, further comprising optical means for focussing the light beam onto a spot between the prongs of said at least first tuning fork.

9. A method according to claim 2, wherein said at least one further tuning fork is arranged behind said at least first tuning fork.

10. A method according to claim 3, wherein said step of separately turning the light source is performed subsequent to said tuning the light source.

11. A photoacoustic detector according to claim 6, wherein said at least one second tuning fork is arranged behind said at least first tuning fork.

* * * * *